(12) United States Patent
Hunnell et al.

(10) Patent No.: US 6,780,380 B2
(45) Date of Patent: Aug. 24, 2004

(54) TISSUE PROCESSOR

(75) Inventors: Jack E. Hunnell, Durham, NC (US); Sergio Cometto, Morrisville, NC (US)

(73) Assignee: Triangle Biomedical Sciences, Inc., Durham, NC (US)

( * ) Notice: Subject to any disclaimer, the term of this patent is extended or adjusted under 35 U.S.C. 154(b) by 545 days.

(21) Appl. No.: 09/761,606

(22) Filed: Jan. 16, 2001

(65) Prior Publication Data

US 2002/0131896 A1 Sep. 19, 2002

(51) Int. Cl.[7] ................................................. B05C 3/02
(52) U.S. Cl. ......................... 422/99; 118/429; 118/688; 427/2.11; 436/176
(58) Field of Search ........................ 427/2.11, 4; 436/8, 436/18, 174, 176; 422/99; 118/52, 688, 696, 600, 602, 603, 408, 429

(56) References Cited

U.S. PATENT DOCUMENTS

| | | | |
|---|---|---|---|
| 2,157,875 A | | 5/1939 | Weiskopf |
| 2,341,198 A | | 2/1944 | Weiskopf |
| 2,386,079 A | | 10/1945 | Weiskopf |
| 2,681,298 A | | 6/1954 | Ferrari |
| 2,684,925 A | | 7/1954 | Ferrari |
| 2,959,151 A | | 11/1960 | Ehrlich |
| 3,227,130 A | | 1/1966 | Weiskopf |
| 3,400,726 A | | 9/1968 | Bernard Du Grail |
| 3,526,203 A | | 9/1970 | Kinney et al. |
| 3,771,490 A | | 11/1973 | Kinney et al. |
| 3,818,747 A | * | 6/1974 | Van Riemsdijk et al. ..... 74/436 |
| 3,889,014 A | | 6/1975 | Kinney et al. |
| 3,892,197 A | * | 7/1975 | Kinney et al. ............... 118/667 |
| 3,972,350 A | | 8/1976 | Pickett |
| 3,982,862 A | | 9/1976 | Pickett et al. |
| 4,141,312 A | * | 2/1979 | Louder et al. ............... 118/702 |
| 4,483,270 A | * | 11/1984 | Toya et al. .................. 118/694 |
| 4,688,517 A | | 8/1987 | Hollman |
| 4,834,943 A | | 5/1989 | Yoshiyama |
| 4,844,870 A | * | 7/1989 | Rasmussen et al. ..... 422/82.05 |
| 5,354,370 A | | 10/1994 | Schmehl |
| 5,389,339 A | * | 2/1995 | Petschek et al. ............... 422/64 |
| 5,560,956 A | | 10/1996 | Schmehl |
| 5,968,436 A | | 10/1999 | Takezaki |
| 6,058,788 A | | 5/2000 | Thiem et al. |
| 2001/0055799 A1 | * | 12/2001 | Baunoch et al. ......... 435/286.5 |

\* cited by examiner

*Primary Examiner*—Jan M. Ludlow
(74) *Attorney, Agent, or Firm*—Steven J. Hultquist; Tristan A. Fuierer; Marianne Fuierer

(57) ABSTRACT

An automatic tissue processor for processing tissue samples for histological analysis. The tissue processor in one configuration includes a retort chamber, a wax storage chamber holding multiple wax containers, a reagent storage chamber holding multiple reagent containers, and a fluid transporting system including a rotary valve operated by a Maltese Cross gear, for selectively connecting the retort chamber with a particular wax or reagent container to supply wax or reagents to the retort chamber. Differential heating of the wax chamber is accommodated by multiple heating elements, with indirect heating of the rotary valve and the fluid transporting system. A computerized central control system for automatic monitoring and control of such tissue processor is advantageously arranged to execute a reagent management program, which enables the central control system to automatically manage reagent usage and replacement.

36 Claims, 6 Drawing Sheets

TISSUE PROCESSOR

BACKGROUND OF THE INVENTION

1. Field of the Invention

The invention relates to an improved automatic tissue processor for processing tissue samples for histological analysis.

2. Description of the Related Art

U.S. Pat. No. 6,058,788 describes a tissue processor apparatus featuring a plurality of containers arranged one beside the other and a complex mechanical mechanism for moving tissue samples from one container to the next. Object holders fastened on lifting means are positioned over the containers. The lifting means include a turntable and a rotatably mounted guide rod translated by drive means in a direction perpendicular to the direction of rotation of the turntable. This tissue processor device is complex in character and costly to operate and maintain.

U.S. Pat. No. 4,834,943 describes a tissue processor apparatus for preparing resin-impregnated specimens for microscopic examination. This apparatus comprises a stack of embedding boxes, each containing a specimen, to which specimen preparation reagents are fed by a delivery pump. The specimen preparation reagents fed to the stack are shaken by a reagent shaker mechanism.

U.S. Pat. No. 4,688,517 describes a tissue processor apparatus including a rotatable table, which carries either the samples or solutions in which the samples are to be immersed. The apparatus comprises complex mechanical mechanisms for rotating the table and causing the table to move up and down. This tissue processor device is mechanically cumbersome and costly to manufacture and maintain.

U.S. Pat. No. 3,889,014 describes a tissue processor programmed for fixation, dehydration and clearing of tissue specimens, utilizing a porous receptacle for each specimen and a processing chamber adapted to contain a plurality of the receptacles. The chamber is connected to a plurality of containers, some of which are refrigerated, and which contain various processing solutions. The solutions are individually piped to the chamber through a remotely controlled valve and manifold associated with a metering pump. This arrangement is reported to minimize fluid contamination and allow each solution to be precisely metered, brought to, retained in and drained from the chamber, to enable specimens to be contacted with reagent solutions according to an automatic programmed time sequence. The program may be varied as to number of cycles per solution, as to the number of solutions per program, as to time per cycle and as to starting and terminal solutions in the program. This tissue processor suffers from clogging and associated problems attributable to inconsistent heating of wax containers and deficiencies in the complex apparatus used to transfer heated wax to the processing chamber.

Other examples of tissue processor technology are described in U.S. Pat. Nos. 3,526,203; 3,771,490; 3,227,130; 2,959,151; 2,386,079; 2,341,198; 2,157,875; 2,959,151; 3,400,726; 2,681,298; and 2,684,925.

Against the background of the above-described state of the art, there is a need in the art for an improved tissue processor that is economical to manufacture, operate and maintain, is highly efficient in operation, employing precision control hardware and software for the execution of tissue processing protocols, without the need for operator intervention during the execution of such protocols.

There is also a need in the art for a tissue processor with an improved heating system for reducing energy consumption and enhancing heating uniformity throughout the system.

There is additionally a need in the art for a tissue processor utilizing a reagent management program for reducing reagent consumption and improving tissue quality.

There is further a need in the art for a tissue processor with an improved fluid transporting system for effective prevention of clogging, reagent carry-over, and other associated problems characteristic of current tissue processor systems.

SUMMARY OF THE INVENTION

The present invention in a broad aspect relates to a tissue processor, comprising:

(a) a retort chamber for processing tissue;

(b) a wax storage chamber comprising one or more wax containers;

(c) a reagent storage chamber comprising one or more reagent containers;

(d) a fluid transporting system communicatively connected with the retort chamber, said fluid transporting system comprising a selector for selectively connecting the retort chamber with any one of the wax containers or the reagent containers; and (e) multiple heating elements for heating the retort chamber, the wax storage chamber, and all or any parts of the fluid transporting system;

(f) a pumping system communicatively connected with the retort chamber for pneumatically driving fluid into or out of the retort chamber via said fluid transporting system; and (g) a computerized central control system for automatic monitoring and managing components (a)–(f).

In a specific embodiment of the present invention, the wax containers and reagent containers are interchangeable plastic bottles that are configured to be installed in slots in their respective storage chambers. Each container may comprise a quick-connect device for establishing fluid communication from such container to the selector of the fluid transporting system, so that such container can be selectively connected to the retort chamber.

In another embodiment of the present invention, the selector of the fluid transporting system comprises a rotary valve controlled by a Maltese Cross gear. Such Maltese Cross gear only allows the rotary valve to rest at a set of predetermined positions. Each of these predetermined positions aligns the rotary valve to form a fluid communication path that connects a particular wax or reagent container with the retort chamber, so that wax or reagent will be supplied to the retort chamber from the particular container.

The position of the rotary valve can be readily monitored by a position sensor mounted on the body of the rotary valve. Moreover, such position sensor can be operative coupled to the computerized central control system for outputting information about position of the rotary valve. An operator can also input command through the central control system to instruct the selector to rotate the rotary valve to a desired position, thereby supplying fluid from a particular container to the retort chamber.

In a further embodiment of the present invention, the wax storage chamber and the fluid transporting system are positioned in a unitary housing so that they can be co-heated by a common set of heating elements. Alternatively, the fluid transporting system can be indirectly heated by heating elements mounted on the wax storage chamber, which is particularly advantageous for preventing overheating of the fluid transporting system and for reducing overall energy consumption.

In order to prevent wax from clogging, the retort chamber, the wax storage chamber, and/or the fluid transporting system are heated to a temperature sufficient for maintaining wax contained therein in a liquid state, with the temperature being controlled to avoid burning the wax.

In order to achieve effective heating and thermal control of the wax storage chamber, a multiplicity, e.g., five to fifteen, of heating elements are preferably mounted in and around the wax storage chamber. These heating elements can be generally divided into three groups: (a) internal heaters placed between each two wax containers inside the wax storage chamber, preferably in a separator used to separate wax containers from each other; (b) external heaters on each side wall as well as the floor of the wax storage chamber; (c) supplemental heaters on each side wall of the wax storage chamber, provided that such side wall is proximate to the fluid transporting system, for promoting co-heating or indirect heating of the fluid transporting system.

In a further aspect of the present invention, the computerized central control system comprises means for monitoring and controlling pressure and/or temperature within the retort chamber. Such means may include, but is not limited to, thermostats, thermocouples, temperature sensors, thermometers, etc.

In yet another aspect, the computerized central control system has reagent management capability, via execution of a reagent management software program.

The reagent management program enables the central control system to perform various tasks relating to effective reagent management. For example, the central control system can store the number of uses of each reagent in its memory, and whenever a particular type of reagent is needed for processing tissues, the central control system instructs the tissue processor to use the least used reagent within that type, which (as the least used) is the cleanest available. The central control system can also output information regarding available wax and reagents loaded in the tissue processor, so that operator of such tissue processor will be able to timely refill wax and reagents when necessary. Specifically, the central control system in one embodiment is arranged to detect a need for replacement of wax or reagent in a wax or reagent container, according to operational limits that are predetermined or otherwise specified by the operator, and to communicate such need to the operator through an output device. Such output device may include any audio or visual display known in the art.

The reagent management program, in a specific embodiment of the present invention, enables the central control system to accept and store input by an operator, which defines operational limits regarding usage of wax or reagent. Preferably, such operational limits are container-specific. More preferably, such operational limits correlate to the amount of tissue specimens processed by wax or reagent from a specific container, evaluated by: (1) the cumulative weight of specimens processed (with each specimen being assigned a weighting factor, depending on its size); (2) the number of tissue processes conducted and/or the number of tissue cassettes processed.

The central control system of the present invention may accept commands from the operator to zero the number of processes conducted and/or the number of cassettes processed by one or more containers, so that the operator may reinitiate the reagent management program after replacing or renewing reagents in all containers.

Alternatively, the central control system may automatically act, without the operator's intervention, to zero the above numbers, when the mode of the reagent management program has been changed (e.g., from a single container mode to a group container mode, as described more fully hereinafter), or when the operator activates or deactivates the reagent management program, or when the operator modifies a definition of a reagent group and/or a limit of a reagent group.

When performing reagent management tasks, the central control system may operate in either a single container mode or a group container mode.

In a single container mode, the central control system manages each fluid container as a separate entity, assigning a defined usage limit to each container depending on what type of reagent it contains. When the defined usage limit of a particular container is reached, the central control system outputs an indication that such limit is reached. Optionally, the central control system prompts replacement of such container automatically.

In a group container mode, each container is managed as a member of a container group containing the same or similar type of reagents, and each group is assigned a defined usage limit depending on what type of reagents it contains. The central control system thereafter monitors usage of each reagent in a particular container group and instructs the processor to use reagents according to an order, so that for each tissue process, the least used reagent (i.e. the cleanest) is used first. When the usage limit for a particular container group is reached, the central control system outputs an indication that the limit is reached. Optionally, the central control system prompts replacement of the most used reagent (i.e., the dirtiest).

In another aspect of the present invention, the central control system is capable of executing a reverse processing program to instruct the tissue processor to reverse-process a tissue sample that has already been processed. Such reverse processing program enables to the tissue processor to unprocess unsatisfactory samples and to reduce tissue damage or waste. Preferably, the central control system, when executing such reverse processing program, instructs the tissue processor to execute steps of a tissue processing protocol in reverse order, starting at the last non-zero time of such protocol.

In a further aspect of the present invention, the pumping system of the tissue processor is configured to alternatively depressurize and pressurize the retort chamber to effectuate fluid flow into and out of the retort chamber. Specifically, the pumping system forces wax or reagent to flow into the retort chamber from a wax or reagent container via the fluid transporting system, by draining air out of the retort chamber to lower pressure in the retort chamber to below the ambient. Alternatively, the pumping system pumps air into the retort chamber to raise pressure therein to above the ambient, thereby forcing wax or reagent out of the retort chamber back into the wax or reagent container via the fluid transporting system.

The tissue processor of the present invention may further comprise one or more purge reagent containers capable of being selectively connected to the retort chamber by the selector of the fluid transporting system, for purging the retort chamber to remove wax residue therefrom.

In still another aspect of the present invention, the tissue processor comprises at least one wax purification device, which functions to bubble air through the wax containers and remove volatile contaminants from the wax.

In yet another aspect, the tissue processor comprises a filtering system for removing contaminants from air discharged by the tissue processor so as to reduce undesirable exhaust fumes.

Other aspects, features, and embodiments of the invention will be more fully apparent from the ensuing disclosure and appended claims.

DETAILED DESCRIPTION OF THE INVENTION AND PREFERRED EMBODIMENTS THEREOF

The present invention relates to an improved automated tissue processor for processing tissue samples in preparation for subsequent histological analysis.

Figure 1:
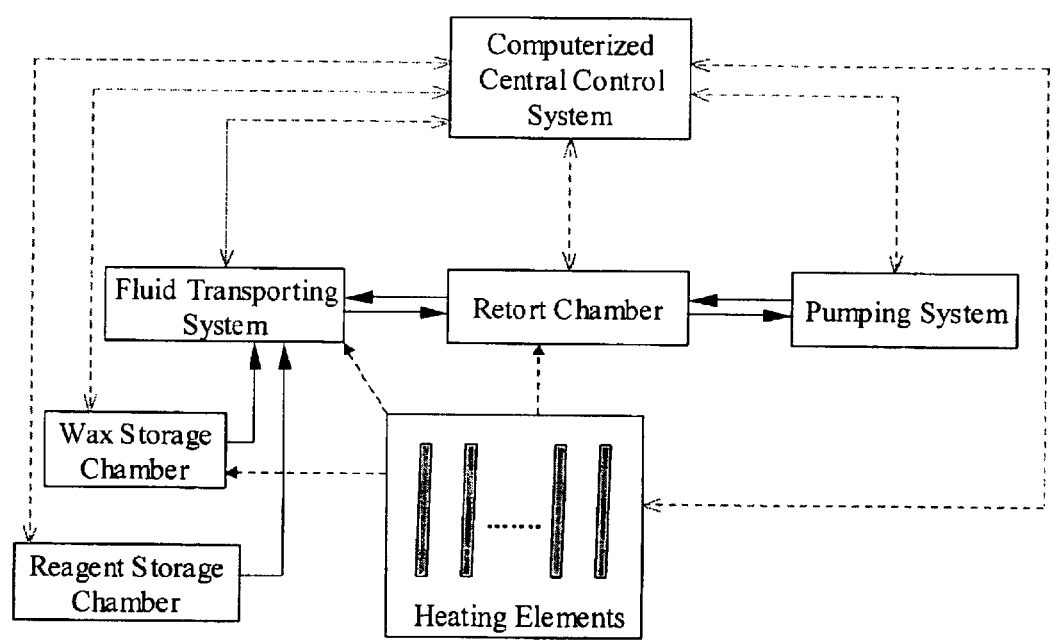
FIG. 1. Generalized schematic of basic components of the tissue processor of the invention.

FIG. 1 shows a generalized schematic representation of core components of the tissue processor of the invention. The tissue processor comprises (1) a retort chamber, (2) a pumping system, (3) a fluid transporting system, (4) a wax storage chamber, (5) a reagent storage chamber, (6) multiple heating elements, and (7) a computerized central control system.

Retort Chamber

The retort chamber comprises a pressure/vacuum-sealed, temperature-controlled housing in which tissue specimens are processed, i.e., water is removed from the specimen and replaced by a wax, such as paraffin.

The retort chamber generally has an opening allowing access to the interior thereof to permit the placement of samples into the chamber. The retort chamber also comprises a sealing device, such as a lid or cap, for sealing the chamber in a manner that permits the pressure inside the chamber to be raised and lowered, in relation to ambient air pressure. The retort chamber also comprises air and fluid ports, permitting air and liquids such as wax or reagents to flow into and out of the chamber when the chamber is otherwise sealed.

The housing and all wetting parts of the retort chamber are preferably constructed from a material that is not readily susceptible to corrosion when contacted with the tissue processing chemicals with which the tissue processor is to be operated. Materials useful for fabricating the retort chamber housing include, but are not limited to, nickel-plated aluminum, nickel-plated brass, and stainless steel.

One or more heating elements are advantageously employed to provide thermal energy to the retort chamber to maintain wax therein in a free-flowing state.

Preferably, the pressure and temperature of the retort chamber are monitored and controlled by one or more thermostats or temperature sensors, and most preferably, such thermostats or temperature sensors are connected to the central control system for improved process control. In such manner, the tissue processor can process specimens requiring different processing pressures. Tissue processing temperatures within the retort chamber are readily maintained at an operator-selected level with a high degree (e.g., ±1° C.) of accuracy.

Pumping System

The pumping system of the present invention generally comprises an air pump, one or more valves, pressure transducers, and associated tubing, functioning together to pump air into or drain air out of the retort chamber, thereby, for example, pneumatically driving wax or reagents out of the retort chamber (if air is pumped into it) or sucking wax or reagents into such chamber (if air is drained from it).

Moreover, the pumping system can be used, with an otherwise-closed retort chamber, to provide negative or positive pressure in such chamber for processing of tissue samples that have to be processed under pressures lower than or above ambient pressure, for example, to improve infiltration of paraffin into the tissue samples. The pumping system is also responsible for removing undesirable vapors from air exhausted by the tissue processor and for preventing overfills in the retort chamber.

The pumping system may comprise a pressure sensor operatively connected to the computerized central control system for determining the level of fluid in the retort chamber.

Fluid Transporting System

The fluid transporting system comprises various tubing and valves, constructed and arranged for selectively establishing a path of fluid communication from one or more wax or reagent containers in the wax or reagent chambers to the retort chamber, and for selectively filling and draining the retort chamber with wax or reagent.

Preferably, the fluid transporting system comprises a single motor-actuated rotary valve for selecting which wax or reagent is to be flowed into the retort chamber. The use of such rotary valve significantly reduces mechanical complexity generally inherent in a multi-fluid transporting system. Examples of useful rotary valves that are amenable to use in the tissue processor of the present invention include those of U.S. Pat. Nos. 4,001,460, 3,972,350, and 3,892,197, the disclosures of which hereby are incorporated by reference herein.

More preferably, the rotary valve is controlled and actuated by a motor assembly, which comprises an AC motor, a Maltese Cross gear actuator that is directly bolted to the rotary valve body and allows the rotary valve to come to rest only at a set of predetermined positions, and a planetary gear set operationally connecting the drive shaft of the AC motor with the Maltese Cross gear actuator.

The position of the rotary valve may be monitored by a position sensor. In a preferred embodiment, this position sensor comprises a binary encoder (as described hereinafter in greater detail).

Wax/Reagent Storage Chambers and Containers

The wax storage chamber maintains processing wax, such as paraffin, at a suitable temperature, typically in the range from about 54° C. to about 60° C., so that the wax is maintained in a melted condition as a free-flowing liquid, and yet not burned. Correspondingly, the wax storage chamber is configured to maintain such suitable temperature uniformly throughout the chamber.

Preferably, the wax storage chamber is heated by a set of separate heating elements, divided into three groups:

internal, external, and supplemental heaters. In a preferred embodiment, each group of heaters is controlled by a separate relay on a relay board in the central control system. More preferably, each group of heaters has a separate duty cycle, and PID (Protocol Identifier) controller parameters with different values. This configuration of "differential heating" enables the system as a whole to maintain the entire wax storage chamber at a constant temperature using a minimal number of temperature sensors and safety thermostats (e.g. one temperature sensor and three safety thermostats).

Another important aspect of the present invention is that the wax and reagent storage chambers comprise disposable, ready-to-use, rapidly removable wax and reagent containers. These containers are preferably interchangeable plastic bottles, configured to be installed in slots in their respective storage chambers.

More preferably, these containers comprise quick-connect devices that can be connected with the fluid transporting system for immediate establishment of a fluid communication path from such containers to the retort chamber via the fluid transporting system.

The wax and reagent containers may be pre-filled, or they may be filled and refilled by the operator. At any time, the operator can switch between reusable and pre-filled containers.

The containers may be made of any suitable plastics. Preferably, they are made of a plastic that is chemically compatible with the wax and reagents used by the tissue processor. 100% HDPE (high-density polyethylene) is preferred.

Such wax and reagent containers with quick-connect devices simplify and expedite the procedure of replacing spent wax and reagents. Moreover, such containers minimize the operator's exposure to toxic reagents during reagent replacement and thereby add a measure of safety that is not found in currently available tissue processors.

Heating Elements

The heating elements of the tissue processor selectively provide thermal energy to the retort chamber, the wax storage chamber, and all or part of the fluid transporting system to keep wax in a liquid state, in order to effectuate free flow of the wax therein and to prevent clogging.

The heating elements useful in the practice of the present invention may be of any suitable type known in the art, including, but not limited to, electrical heaters, radiators, resistance heating tapes, conductive heating elements, heat pipe elements, radiant heating elements, heat transfer coils, convective heating elements, etc.

Computerized Central Control System

The computerized central control system comprises hardware and software necessary for monitoring and managing all the other components of the tissue processor. It preferably comprises a microprocessor or a personal computer for processing and analyzing data received from various monitoring devices and sending instructions to various controlling devices. Moreover, such central control system may comprise input and output means to establish an operator interface and to facilitate operator-participated process control. The input means may be a keyboard, a touch-screen controller, a voice-activated input accessory, or other known inputting devices known in the art. The output means may be embodied in any of a wide variety of known output forms, for example, storage in an accessible file, audio or visual display on an output device, etc. In a preferred embodiment, the output is displayed on a computer monitor.

The central control system is used to control one or more, preferably all, of the power connections and the circuitry that transmits the power to various other components of the tissue processor such as heaters, air pump, valves, sensors, etc.

In a preferred embodiment of the present invention, the central control system is capable of executing a reagent management program (hereinafter RMS). The RMS of the present invention is a system that punctually and precisely manages all reagents to enhance processing consistency and improve sample quality. The use of the RMS provides quality assurance documentation of reagent container status, resulting in substantial time-savings and reducing the possibility of errors when multiple operators use the tissue processor.

The RMS enables the central control system to accept input from an operator defining operational limits regarding usage of wax or reagent. Such operational limits will subsequently determine the frequency of reagent replacement.

In a preferred embodiment, an operational limit is assigned to each container, based on the Cumulative Weight of specimen processed using reagent from the container. First, the central control system assigns each histological specimen a weighting factor, depending on its size. The throughput of the tissue processor is monitored and recorded during the process, by adding up the weight factor of each sample processed to obtain the Cumulative Weight of specimens processed for each container. A signal is subsequently actuated when the Cumulative Weight of a container exceeds a predetermined limit, usually set by the operator. The central control system optionally prompts the replacement of reagent in that container.

In an alternative embodiment, the operation limit is assigned based on the number of tissue processes conducted or the number of tissue cassettes processed. Preferably, the operator-assigned limits include both a limit based on the number of processes conducted and a limit based on the number of cassettes processed; when both limits of a container are reached or exceeded, the central control system will suggest or require replacement of the reagent for that specific container.

In a specific embodiment, the RMS enables the central control system to operate in a single container mode, in which each container is managed as a separate entity. In single container mode, each container will have a defined usage limit depending on the specific type of reagent it contains. In this mode, the number that identifies the physical position of the container in the processor corresponds with the program step number, which is usually the same as the identification number of such container.

The RMS also enables the central control system to operate in an alternative mode, a group container mode, to perform its reagent management tasks. In this mode, reagent containers are divided into groups based on the type of reagent contained in the containers, and each reagent container is managed as member of a group of similar reagents.

As a specific example, the central control system may categorize reagents into one of the following six groups: (1) not defined; (2) fixative; (3) low grade dehydrant; (4) high grade dehydrant; (5) clearing; and (6) paraffin wax.

Each group then is assigned a defined usage limit depending on the specific type of reagent involved. The central control system subsequently monitors usage of each reagent container in a particular group, and determines an order for the containers based on the frequency of use, from the least to the most. When the tissue process needs reagent from the particular group, the central control system will direct it to use reagent according to the determined order, so that each time reagent in the least used container (i.e. the cleanest) will be used first. Moreover, when the usage limit of the group is reached, the central control system informs the operator that replacement is needed, and optionally prompts replacement of reagent in the most used (i.e., the dirtiest) container.

An illustrative example of the group mode performance using a portion of the routine reagents by the tissue processor of the present invention is now described. High grade dehydrants are placed in bottles 6, 7 and 8, which are classified as one group. The operational limits of this group are fixed as one process. The sequence of use would be the following:

| Step | Usage |
| --- | --- |
| PROCESS #1 | |
| 6 | Bottle 6 (fresh reagent) |
| 7 | Bottle 7 (fresh reagent) |
| 8 | Bottle 8 (fresh reagent) |
| PROCESS #2 | |
| 6 | Bottle 7 |
| 7 | Bottle 8 |
| 8 | Bottle 6 (fresh reagent) |
| PROCESS #3 | |
| 6 | Bottle 8 |
| 7 | Bottle 6 |
| 8 | Bottle 7 (fresh reagent) |
| PROCESS #4 | |
| 6 | Bottle 6 |
| 7 | Bottle 7 |
| 8 | Bottle 8 (fresh reagent) |

In this example, after the third process, the reagent group sequence will correspond again to the physical position of the bottles and to the step of the program. For the paraffin group, which in a preferred embodiment includes 4 bottles, the frequency of a return to the physical order is 4 processes.

The group mode advantageously facilitates maintenance, management and quality assurance by managing the containers according to operator-defined classification of the reagent, automatically selecting the proper order of usage based on cleanliness of reagent in the containers, and reminding the operator to replace reagents in those containers that have reached their defined use limits.

The system is also preferably programmed to permit postponement of the substitution of reagents until after a process has been completed. In a specific embodiment, the escape (ESC) key on the keyboard of the tissue processor is pressed to skip this session of the RMS and postpone it until the end of the next process, and at the end of the next process, the central control system will prompt the operator again to replace the reagents that expired at the end of the previous processes plus those whose limits have been reached after the most recent process.

When in the group mode, the central control system preferably is programmed to prompt the replacement of reagents with symbolic indicators (e.g., graphics and/or text). More preferably, the container to be replaced is indicated by a graphical indication of a corresponding container on a graphical representation of the tissue processor on the computer monitor.

Figure 2:
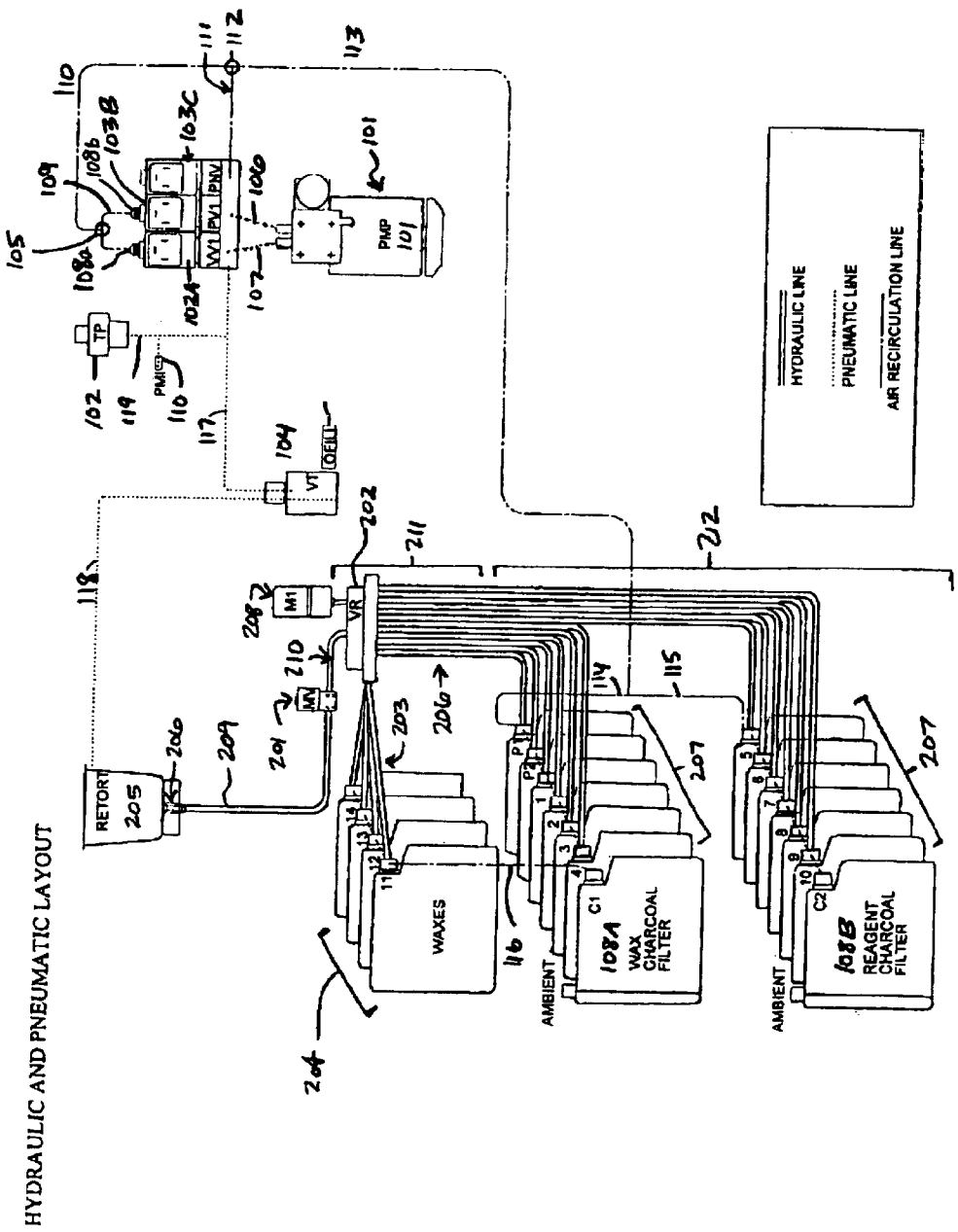
FIG. 2. Generalized schematic diagram illustrating the pumping system, the retort chamber, the fluid transporting system, and the wax and reagent containers.

FIG. 2 shows a generalized schematic diagram illustrating the pumping system, the retort chamber, the fluid transporting system, and the wax and reagent containers.

The major components of the pumping system include the air pump 101, a group of solenoid valves 103A, 103B, and 103C, the pressure transducer 102, and the overfill container 104.

The air pump 101 is used to lower or raise the pressure in the retort chamber 205 and is arranged in fluid communication with the retort chamber 205 via pneumatic lines 106, 117, and 118, so that air may be pumped into or out of the retort chamber 205. The pumping system may be arranged to permit stored air and/or atmospheric air to be pumped into the retort chamber from an air source, while air exiting the retort chamber may be redirected to an effluent path or an effluent abatement system. Air discharged from the retort chamber 205 is preferably recirculated via air recirculation line 107 to a pair of cleaning filters 108a and 108b.

The air pump 101 is preferably a piston-type reciprocating pump, driven by a capacitor motor (not shown). The air pump may suitably be mounted, e.g., by mechanical attachment means, such as screws, nuts, bolts, threaded posts, etc., on one or more vibration damping mounts.

The pumping system also comprises a pressure transducer 102 for monitoring pressure of the air.

To fill the retort chamber with air, a main valve 201 of the fluid transporting system, between the retort chamber 205 and the wax and reagent storage chambers 211 and 212, is opened, thereby establishing an open path of fluid communication from the retort chamber into the wax and reagent storage chambers. Air is then pumped by the air pump 101 through pressure valve 103B and air lines 117 and 118, into the retort chamber, forcing fluid in the retort chamber to be discharged from it via the fluid transporting system, and flowed back into the wax and reagent storage chambers.

By closing the main valve 201, the pumping system can also be used to pressurize the retort chamber. A pressure detector (not shown) is operatively coupled to the retort chamber 205 to determine when the chamber has reached the desired pressure, at which point the central control system will correspondingly adjust the air pump 101.

To drain air out of the retort chamber 205, the air pump 101 extracts air from the retort chamber through communicating lines 118 and 117. By such action, wax and reagent are forced out of the wax and reagent storage chamber 211 and 212 through the fluid line 210, main valve 201, and fluid line 209 of the fluid transporting system, into the retort chamber 205. By closing the main valve 201, this flow path can also be used to create a vacuum in the retort chamber.

Set out below is a key to the numerical designations of the components shown in FIG. 2:

| Reference Number | Component(s) |
| --- | --- |
| 1 . . . 10 | reagents containers |
| 11 . . . 14 | wax containers |
| P1, P2 | purge reagents |
| C1, C2 | charcoal filters |
| MV | main valve |
| M1 | rotary valve motor |
| VR | rotating valve |
| OFILL | overfill sensor |
| TP | pressure transducer |
| VV1 | vacuum valve |
| PV1 | pressure valve |
| PNV | pressure normalization valve |
| PMP | air pump |
| VT | vapor trap |
| PMI | pressure measurement intake |

Figure 3:
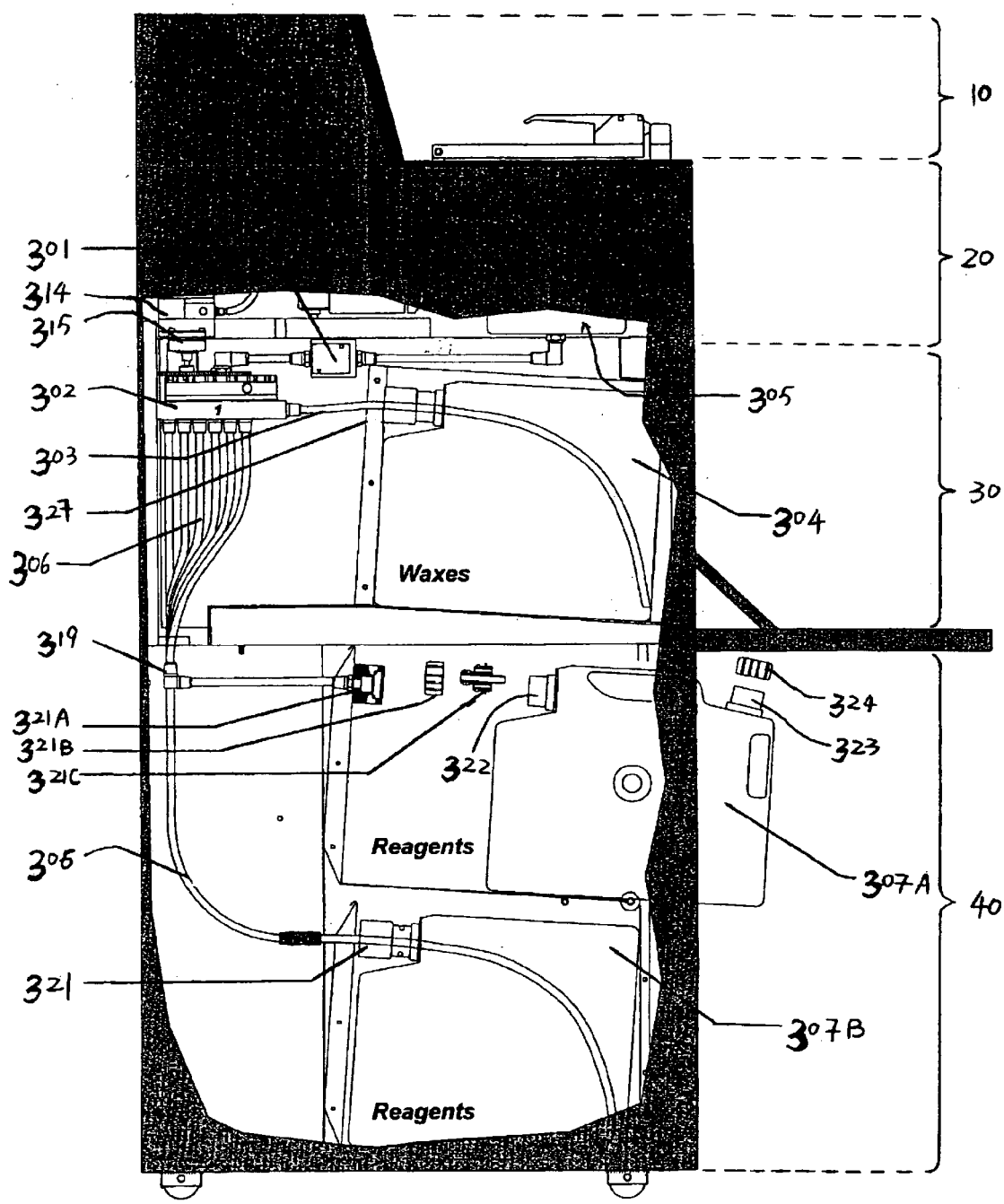
FIG. 3. Side cutaway view of a tissue processor of the present invention, showing components of the fluid transporting system and the wax and reagent containers.

FIG. 3 shows a side cutaway view of a tissue processor according to a preferred embodiment of the present invention.

The wax storage chamber 30 contains a series of wax containers 304, and the reagent storage chamber 40 contains a series of reagent containers 307A and 307B. These containers comprise quick-connect devices 321, so that they can be inserted into the slots 327 of their respective storage chambers in a manner facilitating immediate establishment of a path of fluid communication with the fluid transporting system.

A preferred quick-connect device 321 comprises a female component 321A positioned in the fixed slots 327 in the storage chambers, arranged to engage a male component 321C on the containers. The male component 321C is inserted into the female component 321A to form a seal. The female component 321A may, for example, be mounted on the container 304 or 307A or B by a cap 321B. The male component 321C is fixed to the neck 322 of the container. When properly joined, the male component and the female component together form a path of fluid communication from the bottle into the fluid flow tubing 306 of the fluid transporting system. The male and female components may also be reversed, such that the male component is fixed to the storage chambers and the female component to the containers.

Tubing 206, with fitting 319, connects the containers 304 and 307A, 307B to the rotary valve 302 for selectively establishing a path of fluid communication between the retort chamber 305 and specific containers. The rotary valve 302 may be driven by a valve motor assembly 314 and monitored by a position sensor 315, which is operatively connected to the central control system 10 of the tissue processor.

The rotary valve 302 is then connected the main valve 301 to establish a path of fluid communication from the rotary valve 302 to the interior of the retort chamber 305.

The main valve 301 is interposed in the path of fluid communication extending from the rotary valve to the retort chamber. The main valve is preferably a solenoid type valve, and may for example comprise a VITON® (E. I. DuPont de Nemours and Company, Wilmington, Del.) valve seat. In an alternative and more preferred embodiment, the main valve 301 comprises a sapphire valve seat and is held together with a bowed (sprung) E-type retaining ring.

The main valve 301 operates in conjunction with the pumping system (not shown) for controlling pressure in the retort chamber. By opening the main valve, the pumping system can be used to drain and fill the retort chamber. By closing the main valve, the pumping system can be used to raise or lower pressure in the retort chamber for processing of samples under positive or negative pressure conditions.

Figure 4:
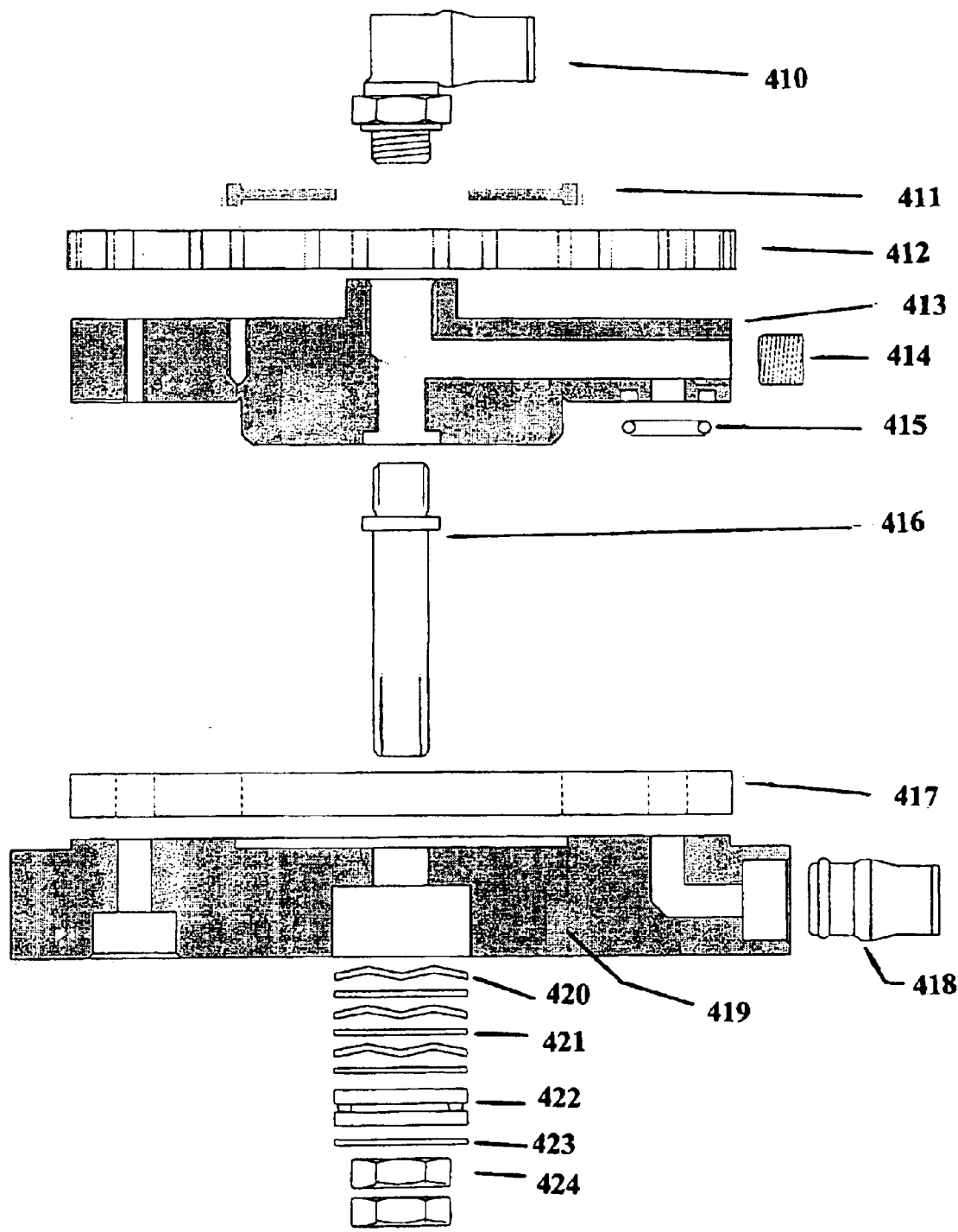
FIG. 4. Exploded view of a rotary valve for use in one embodiment of the invention.

FIG. 4 illustrates a preferred rotary valve for use in the practice of the invention. The rotary valve permits selection of reagent (e.g., cleaning and/or tissue processing reagents) and/or paraffin containers for filling and draining the retort chamber. Any of a variety of rotary valves known in the art may be used for this purpose. The body of the rotary valve is preferably constructed from a material that is not subject to corrosion by reagents used in the processes for which the tissue processor is intended; a preferred material is stainless steel.

The rotary valve preferably comprises a mechanism for maintaining its exact positioning. In a preferred embodiment, this mechanism comprises a "Maltese Cross" gear that is bolted directly to the rotary valve body and allows the valve to come to rest only at certain positions. More preferably, the current position of the rotary valve is monitored by a position sensor, such as a binary encoder, which is connected to the central control system of the tissue processor.

In a preferred embodiment, the rotary valve has two main components, the upper rotary valve section 413 and the lower rotary valve section 419, separated by the seal disk 417. Reagent from a wax container or a reagent container enters via one of several entrance ports in the lower rotary valve section 419 and is discharged therefrom via the exit port into the tubing extending from the exit port to the retort chamber (interrupted by the main valve). The lower rotary valve section 419 is fixed, and the upper section rotates to select the tube through which the liquid will be flowed.

The rotary valve is functionally coupled to a means for rotating the valve. In a preferred embodiment, this means comprises a motor assembly, which preferably is located above the heated rotary valve chamber. The motor assembly preferably comprises an AC motor, the Maltese Cross gear actuator, and a planetary gear set operationally connecting the drive shaft of the AC motor with the Maltese Cross gear actuator. A relay on the control board of the central control system permits the motor to be energized or de-energized by a signal from the central control system. Thus the central control system controls the position of the rotary valve by monitoring its position via the position sensor and controlling the power supply to the rotary valve motor.

Figure 5:
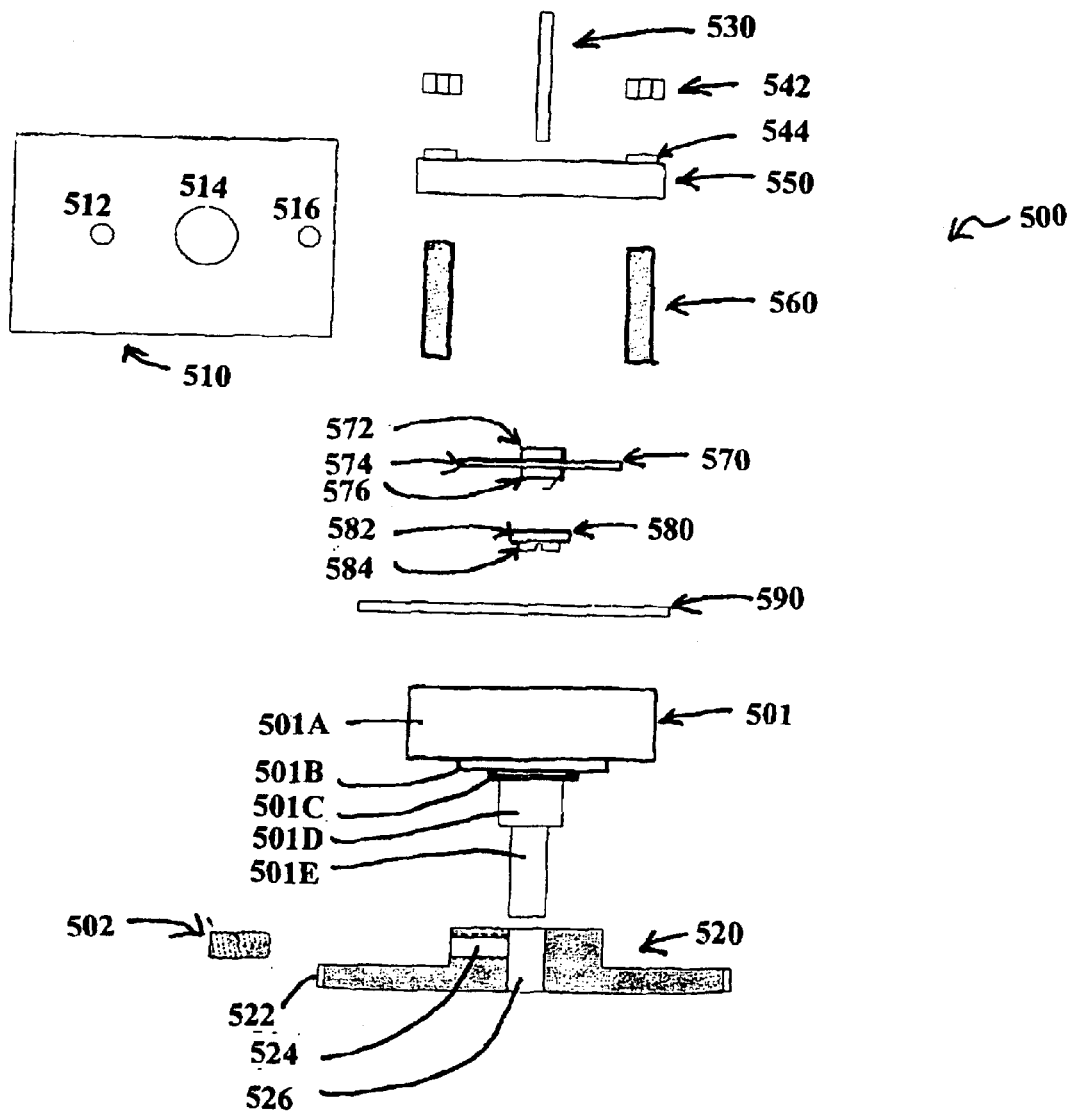
FIG. 5. Exploded view of a position sensor according to one embodiment of the invention.

In a preferred embodiment, a binary encoder with multiple (preferably at least 5) contact wires and at least one common wire yielding multiple (preferably at least 16) combinations of signals, is used as position sensor for the rotary valve. An example of such binary encoder is shown in FIG. 5, comprising a main sensor element 500, an insulating pad 510 formed for example of TEFLON® polytetrafluoroethylene (E. I. DuPont de Nemours and Company, Wilmington, Del.), and a position sensor gear 520.

The encoder circuit board 590 is electronically connected to the central control system, e.g., by a wire harness.

The position sensor 500 is preferably mounted in a housing with a clear cover 550 (e.g., fabricated of clear plastic or other transparent material) to permit the operator/maintainance attendant to see through the housing to ensure that the elements of the sensor 500 are properly aligned, e.g., to be certain that the rotating encoder element is properly centered and riding on the bearing 580. The position sensor gear 520 is configured to mate with the position sensor shaft 501 and maintained in position using one or more screws 502.

The flat pinion 530 is inserted through the housing 550 and extends through the encoder circuit board 590 into the bearing/shaft housing 501, to align the overall assembly.

Screws 560, with nuts 542 and washers 544, are used to support the bearing/shaft housing, and extend through such housing.

The central control system preferably comprises automated means for testing and calibrating the rotary valve position sensor. In a preferred embodiment, the central control system is capable to provide a menu for executing programs for technical analyses of the operation of the tissue processor. The central control system is preferably programmed to provide output indicating the position of the rotary valve system, and to accept input directing power to be supplied to the rotary valve motor until the rotary valve rotates to a specified position.

The central control system may also be suitably programmed to permit the operator to manually rotate the position of the position sensor, while observing output indicating the position of the sensor, to ensure that the sensor registers all positions (e.g., in a preferred embodiment, all 16 positions).

Figure 6:
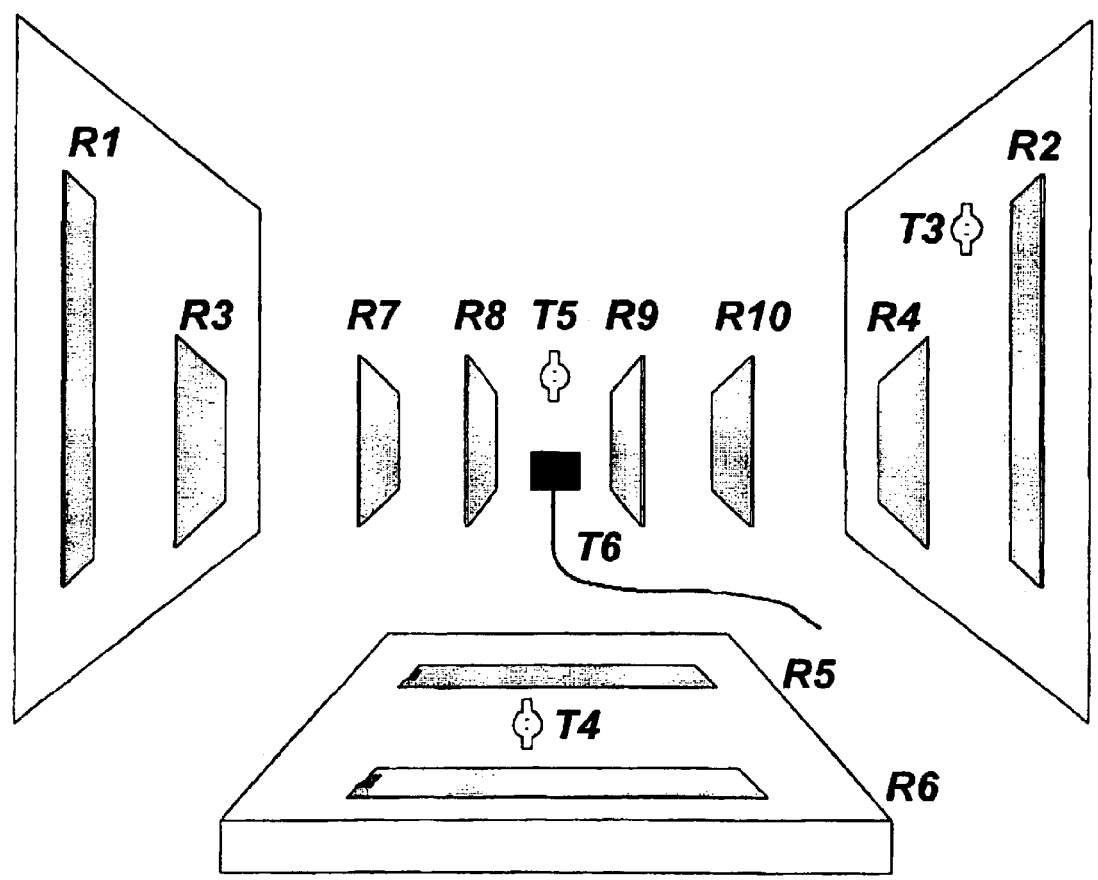
FIG. 6. Schematic diagram showing placement of heaters in the wax module in a preferred embodiment of the invention.

FIG. 6 shows preferred locations of heaters used to heat the wax storage chamber, as follows:

Internal Heaters: located between the wax containers in the warm wax storage chamber, as heaters R7, R8, R9 and R10.

External Heaters: located on each of the side walls and floor of the warm wax storage chamber, as heaters R3, R4, R5 and R6.

Supplemental Heaters: located on each of the side-walls of the wax module chamber, proximate to the fluid transporting system, as heaters R1 and R2.

The tissue processor of the present invention preferably comprises a paraffin wax purification cycle (WPC) that removes xylene contaminant from the wax. The WPC dramatically reduces consumption of wax by bubbling air through the wax containers. The volatile xylene and other volatile contaminants evaporate due to the heating of the wax containers during the WPC process. The air bubbled through the wax carries these vapors out of the system.

EXAMPLE

The tissue processor of the invention has been constructed having the structure and operational features generally described herein, with the following characteristics:

| | |
|---|---|
| Weight | 120 Kg (264 lbs.) |
| Dimension in cm (floor standing version) | H 134 - W 53 - D 60 |
| Sample processing capacity | 300 cassettes |
| Paraffin wax temperature (warm chamber) | 50°/60° C. |
| Paraffin wax temperature (during the process) | 50°/60° C. |
| Reagent temperature (during the process) | Ambient/45° C. |
| Temperature accuracy | +/-1° C. |
| Reagent filling time | 45 seconds |
| Reagent draining time | 30 seconds |
| Pressure range | 300/1350 mBar (ambient = 1000 mBar) |
| Filling pressure | 750 mBar |
| Draining pressure | 1250 mBar |
| Anti-blackout device | The CPU memory is battery backed-up. In the event of a blackout/power outage, the processor reinitiates the process from the interrupted point. In the event a blackout/outage stops the process during a paraffin step, a delay function allows sufficient time for paraffin melting before reinitiating the program. |
| Number of reagents | 10 (each contained in a 2.5 liter bottle) |
| Number of paraffin | 4 (each contained in a 2.5 liter bottle) |
| Pre-heated paraffin | 1 slot |
| Number of purge reagents | 2 (each contained in a 2.5 liter bottle) |
| Number of filters | 2 charcoal (each contained in a 2.5 liter - modified bottle) |

What is claimed is:

1. A tissue processor comprising:
    (a) a retort chamber for processing tissue;
    (b) a wax storage chamber comprising one or more wax containers;
    (c) a reagent storage chamber comprising one or more reagent containers;
    (d) a fluid transporting system communicatively connected with the retort chamber, said fluid transporting system comprising a selector for selectively connecting the retort chamber with any one of the wax containers or the reagent containers;
    (e) multiple heating elements for heating the retort chamber, the wax storage chamber, and all or any parts of the fluid transporting system;
    (f) a pumping system communicatively connected with the retort chamber for pneumatically driving fluid into or out of the retort chamber via said fluid transporting system; and
    (g) a computerized central control system for automatic monitoring and managing components (a)–(f), wherein the central control system is constructed and arranged to execute a reagent management program enabling the central control system to perform at least one operation selected from the group consisting of operations (1), (2), (3), (4) and (5):
        (1) storing the number of uses of each reagent, and when a particular type of reagent is to be used, instructing the tissue processor to use the least used reagent of said type;
        (2) accepting and storing input by an operator defining operational limits regarding usage of wax or reagent, wherein the input comprises an operator-assigned limit for each container based on cumulative weight of tissue specimens processed;
        (3) accepting and storing input by an operator defining operational limits regarding usage of wax or reagent, wherein the input comprises an operator-assigned limit for each container based on the number of tissue processes conducted and/or the number of tissue cassettes processed;
        (4) accepting and storing input by an operator defining operational limits regarding usage of wax or reagent, operating in a single container mode, in which (A) each container is managed as a separate entity, (B) each container is assigned a defined usage limit depending on the specific type of reagent it contains, and (C) when said usage limit of a container is reached, the central control system outputs an indication that the limit is reached, and optionally prompts replacement of the container; and
        (5) accepting and storing input by an operator defining operational limits regarding usage of wax or reagent, operating in a group container mode, in which (A) each container is managed as a member of a container group containing the same or similar type of reagents, (B) each group is assigned a defined usage limit depending on the specific type of reagents it contains, (C) the central control system monitors usage of reagent from each container in a particular group, (D) the containers in such group are used according to an order determined by the central control system so that for each tissue process, reagent from the least used container is used first, and (B) when said usage limit of a group is reached, the central control system outputs an indication that the limit is reached, and optionally prompts replacement of reagent in the most used container.

2. The tissue processor of claim 1, wherein the wax containers and reagent containers are configured to be installed in slots in their respective storage chambers.

3. The tissue processor of claim 2, wherein the wax containers and reagent containers comprise interchangeable plastic bottles.

4. The tissue processor of claim 2, wherein each wax or reagent container comprises a quick-connect device for establishing fluid communication from such container to the selector of the fluid transporting system, so that such container can be selectively connected to the retort chamber.

5. The tissue processor of claim 1, wherein the selector of the fluid transporting system further comprises a Maltese Cross gear mounted to the rotary valve, which only allows the rotary valve to rest at a set of predetermined positions, at each of which the rotary valve is aligned so as to establish a fluid communication path that connects a particular wax or reagent container with the retort chamber.

6. The tissue processor of claim 1, wherein the selector of the fluid transporting system further comprises a position sensor for monitoring a current position of the rotary valve.

7. The tissue processor of claim 6, wherein the position sensor is operatively connected to the central control system to provide data regarding the instant position of the rotary valve.

8. The tissue processor of claim 7, wherein the central control system is capable of receiving a command from an operator and instructing the selector to rotate the rotary valve to a specified position according to said command.

9. The tissue processor of claim 7, wherein the central control system is capable of outputting data regarding the instant position of the rotary valve.

10. The tissue processor of claim 1, wherein the wax storage chamber and the fluid transporting system are coextensively positioned in a unitary housing.

11. The tissue processor of claim 10, wherein the wax storage chamber and the fluid transporting system are co-heated by common heating elements.

12. The tissue processor of claim 10, wherein the fluid transporting system is indirectly heated by heating elements mounted on the wax storage chamber.

13. The tissue processor of claim 1, wherein the retort chamber, the wax storage chamber, and/or the fluid transporting system are heated to a temperature sufficient for maintaining wax in a liquid state without burning said wax.

14. The tissue processor of claim 1, wherein the wax storage chamber is heated by 5 to 15 heating elements.

15. The tissue processor of claim 14, wherein said 5 to 15 heating elements are divided into three groups: internal, external, and supplemental, wherein each group is controlled by its own relay on a relay board, and wherein said heating elements are positioned as follows:
(a) at least one internal heater between each two wax containers inside the wax storage chamber;
(b) at least one external heater on each side wall and floor of the wax storage chamber; and
(c) at least one supplemental heater on each side wall of the wax storage chamber that is proximate to the fluid transporting system.

16. The tissue processor of claim 1, wherein the central control system comprises means for monitoring and controlling pressure and/or temperature within the retort chamber.

17. The tissue processor of claim 1, wherein the reagent management program enables the central control system to perform operation (1).

18. The tissue processor of claim 1, wherein such reagent management program further enables the central control system to output information regarding available wax and reagents loaded in the tissue processor.

19. The tissue processor of claim 1, wherein such reagent management program further enables the central control system to: (1) detect a need for replacement of wax or reagent in a wax or reagent container, according to operational limits that are predetermined or otherwise specified by an operator, and (2) communicate such need to the operator through an output device.

20. The tissue processor of claim 1, wherein such reagent management program enables the central control system to perform operation (2).

21. The tissue processor of claim 1, wherein such reagent management program enables the central control system to perform operation (3).

22. The tissue processor of claim 21, wherein the reagent management program further enables the central control system to accept commands from the operator to zero the number of processes conducted and/or the number of cassettes processed for one or more containers.

23. The tissue processor of claim 21, wherein the reagent management program further enables the central control system to automatically zero the number of processes conducted and/or the number of cassettes processed for one or more containers, when one or more of the following functions are selected:
(a) changing reagent management mode from single container mode to group mode or vice versa;
(b) activating or deactivating the reagent management program; and
(c) modifying a definition of a reagent group and/or a limit of a reagent group.

24. The tissue processor of claim 1, wherein the reagent management program enables the central control system to perform operation (4).

25. The tissue processor of claim 1, wherein the reagent management program enables the central control system to perform operation (5).

26. The tissue processor of claim 1, wherein the central control system is capable of executing a reverse processing program for reverse-processing of tissue samples that have already been processed.

27. The tissue processor of claim 26, wherein the reverse processing program enables the central control system to instruct the tissue processor to execute steps of a tissue processing protocol in reverse order, starting at the last non-zero time of such tissue processing protocol.

28. The tissue processor of claim 1, wherein the pumping system is configured to alternatively:
(a) lower pressure in the retort chamber to below the ambient by draining air out of said retort chamber, thereby forcing wax or reagent to flow into the retort chamber from a wax or reagent container via the fluid transporting system; and
(b) raise pressure in the retort chamber to above the ambient by pumping air into said retort chamber, thereby forcing wax or reagent out of the retort chamber and back into the wax or reagent container via the fluid transporting system.

29. (Original) The tissue processor of claim 1, further comprising one or more purge reagent containers constructed and arranged to be selectively connected to the retort chamber by the selector of the fluid transporting system, for purging the retort chamber with purge reagent to remove wax residues from the retort chamber.

30. The tissue processor of claim 1, further comprising a filtering system for removing contaminants from air discharged by the tissue processor.

31. A tissue processor comprising:
(a) a retort chamber for processing tissue;
(b) a wax storage chamber comprising one or more wax containers;
(c) a reagent storage chamber comprising one or more reagent containers;
(d) a fluid transporting system communicatively connected with the retort chamber, said fluid transporting system comprising a selector for selectively connecting the retort chamber with any one of the wax containers or the reagent containers;
(e) multiple heating elements for heating the retort chamber, the wax storage chamber, and all or any parts of the fluid transporting system;

(f) a pumping system communicatively connected with the retort chamber for pneumatically driving fluid into or out of the retort chamber via said fluid transporting system; and (g) a computerized central control system for automatic monitoring and managing components (a)–(f), wherein the wax storage chamber is heated by 5 to 15 heating elements divided into three groups: internal, external, and supplemental, wherein each group is controlled by its own relay on a relay board, and wherein said heating elements are positioned as follows:

(i) at least one internal heater between each two wax containers inside the wax storage chamber;

(ii) at least one external heater on each side wall and floor of the wax storage chamber; and (iii) at least one supplemental heater on each side wall of the wax storage chamber that is proximate to the fluid transporting system.

32. A tissue processor comprising:

(a) a retort chamber for processing tissue;

(b) a wax storage chamber comprising one or more wax containers;

(c) a reagent storage chamber comprising one or more reagent containers;

(d) a fluid transporting system communicatively connected with the retort chamber, said fluid transporting system comprising a selector for selectively connecting the retort chamber with any one of the wax containers or the reagent containers;

(e) multiple heating elements for heating the retort chamber, the wax storage chamber, and all or any parts of the fluid transporting system;

(f) a pumping system communicatively connected with the retort chamber for pneumatically driving fluid into or out of the retort chamber via said fluid transporting system; and (g) a computerized central control system for automatic monitoring and managing components (a)–(f), wherein the central control system is constructed and arranged to execute a reagent management program that enables the central control system to: (1) store the number of uses of each reagent, and (2) when a particular type of reagent is to be used, instruct the tissue processor to use the least used reagent of said type.

33. A tissue processor comprising:

(a) a retort chamber for processing tissue;

(b) a wax storage chamber comprising one or more wax containers;

(c) a reagent storage chamber comprising one or more reagent containers;

(d) a fluid transporting system communicatively connected with the retort chamber, said fluid transporting system comprising a selector for selectively connecting the retort chamber with any one of the wax containers or the reagent containers;

(e) multiple heating elements for heating the retort chamber, the wax storage chamber, and all or any parts of the fluid transporting system;

(f) a pumping system communicatively connected with the retort chamber for pneumatically driving fluid into or out of the retort chamber via said fluid transporting system; and (g) a computerized central control system for automatic monitoring and managing components (a)–(f), wherein the central control system is constructed and arranged to execute a reagent management program that enables the central control system to accept and store input by an operator defining operational limit regarding usage of wax or reagent wherein the input comprises an operator-assigned limit for each container based on cumulative weight of tissue specimens processed.

34. A tissue processor comprising:

(a) a retort chamber for processing tissue;

(b) a wax storage chamber comprising one or more wax containers;

(c) a reagent storage chamber comprising one or more reagent containers;

(d) a fluid transporting system communicatively connected with the retort chamber, said fluid transporting system comprising a selector for selectively connecting the retort chamber with any one of the wax containers or the reagent containers;

(e) multiple heating elements for heating the retort chamber, the wax storage chamber, and all or any parts of the fluid transporting system;

(f) a pumping system communicatively connected with the retort chamber for pneumatically driving fluid into or out of the retort chamber via said fluid transporting system; and (g) a computerized central control system for automatic monitoring and managing components (a)–(f), wherein the central control system is constructed and arranged to execute a reagent management program that enables the central control system to accept and store input by an operator defining operational limit regarding usage of wax or reagent wherein the input comprises an operator-assigned limit for each container based on the number of tissue processes conducted and/or the number of tissue cassettes processed.

35. A tissue processor comprising:

(a) a retort chamber for processing tissue;

(b) a wax storage chamber comprising one or more wax containers;

(c) a reagent storage chamber comprising one or more reagent containers;

(d) a fluid transporting system communicatively connected with the retort chamber, said fluid transporting system comprising a selector for selectively connecting the retort chamber with any one of the wax containers or the reagent containers;

(e) multiple heating elements for heating the retort chamber, the wax storage chamber, and all or any parts of the fluid transporting system;

(f) a pumping system communicatively connected with the retort chamber for pneumatically driving fluid into or out of the retort chamber via said fluid transporting system; and (g) a computerized central control system for automatic monitoring and managing components (a)–(f), wherein the central control system is constructed and arranged to execute a reagent management program that enables the central control system to accept and store input by an operator defining operational limit regarding usage of wax or reagent, wherein the reagent management program enables the central control system to operate in a single container mode, in which:

(i) each container is managed as a separate entity;

(ii) each container is assigned a defined usage limit depending on the specific type of reagent it contains;

(iii) when said usage limit of a container is reached, the central control system outputs an indication that the limit is reached, and optionally prompts replacement of the container.

36. A tissue processor comprising:
(a) a retort chamber for processing tissue;
(b) a wax storage chamber comprising one or more wax containers;
(c) a reagent storage chamber comprising one or more reagent containers;
(d) a fluid transporting system communicatively connected with the retort chamber, said fluid transporting system comprising a selector for selectively connecting the retort chamber with any one of the wax containers or the reagent containers;
(e) multiple heating elements for heating the retort chamber, the wax storage chamber, and all or any parts of the fluid transporting system;
(f) a pumping system communicatively connected with the retort chamber for pneumatically driving fluid into or out of the retort chamber via said fluid transporting system; and
(g) a computerized central control system for automatic monitoring and managing components (a)–(f), wherein the central control system is constructed and arranged to execute a reagent management program that enables the central control system to accept and store input by an operator defining operational limit regarding usage of wax or reagent, wherein the reagent management program enables the central control system to operate in a group container mode, in which:

(i) each container is managed as a member of a container group containing the same or similar type of reagents;
(ii) each group is assigned a defined usage limit depending on the specific type of reagents it contains;
(iii) the central control system monitors usage of reagent from each container in a particular group;
(iv) the containers in such group are used according to an order determined by the central control system so that for each tissue process, reagent from the least used container is used first; and
(v) when said usage limit of a group is reached, the central control system outputs an indication that the limit is reached, and optionally prompts replacement of reagent in the most used container.

\* \* \* \* \*